United States Patent [19]

Ford et al.

[11] Patent Number: 4,864,045
[45] Date of Patent: * Sep. 5, 1989

[54] PRODUCTION OF AMINOETHYL HYDROGEN SULFATE

[76] Inventors: Michael E. Ford, P.O. Box 277, Trexlertown, Pa. 18087; Thomas A. Johnson, R.D. #1, Bobby La., Orefield, Pa. 18069

[ * ] Notice: The portion of the term of this patent subsequent to Jul. 1, 2003 has been disclaimed.

[21] Appl. No.: 899,682

[22] Filed: Oct. 2, 1986

[51] Int. Cl.$^4$ .......................................... C07C 141/02
[52] U.S. Cl. ............................................................ 558/29
[58] Field of Search ............................................ 558/29

[56] References Cited

U.S. PATENT DOCUMENTS

| | | | |
|---|---|---|---|
| 2,264,759 | 12/1941 | Jones | 260/453 |
| 2,971,936 | 2/1961 | Dubien et al. | 558/29 |
| 3,037,042 | 5/1962 | Laemmle | 260/458 |
| 3,133,950 | 5/1964 | Pizzarello et al. | 260/458 |
| 3,153,079 | 10/1964 | Forshaw | 260/458 |
| 3,169,143 | 2/1965 | Gavlin et al. | 260/458 |
| 3,194,826 | 7/1965 | Goldstein et al. | 260/458 |
| 3,337,633 | 8/1967 | Schmitt et al. | 260/586 |
| 3,763,208 | 10/1973 | Sowerby | 260/458 |
| 4,330,480 | 5/1982 | Hertel et al. | 260/458 |

*Primary Examiner*—Nicky Chan

[57] ABSTRACT

Aminoethyl hydrogen sulfate is produced under acidic conditions by reating ammonium bisulfate or ammonium sulfate with an ethylene compound represented by either of the formulae:

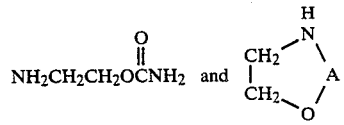

where A represents C=C or C=S.

7 Claims, No Drawings

PRODUCTION OF AMINOETHYL HYDROGEN SULFATE

This is a continuation of application Ser. No. 586,911, filed Mar. 9, 1984, now abandoned.

TECHNICAL FIELD

This invention pertains to the synthesis of aminoethyl hydrogen sulfate which is a useful intermediate in the synthesis of textiles, dyes, pharmaceuticals and polyamines.

BACKGROUND OF THE INVENTION

Typically, sulfuric acid esters of amino alcohols including ethanolamines have been produced by reacting hydroxy aliphatic or cyclic alkanolamines with concentrated sulfuric acid or sulfur trioxide. Water is formed in the reaction with sulfuric acid, and, in order to drive the reaction to completion, the water must be removed. Representative patents which illustrate the formation of sulfuric acid esters of amino alcohols by reaction of amino alcohols with sulfuric acid or sulfur trioxide and illustrate techniques for effecting removal of the water during the reaction for the amino aliphatic and cyclic hydrogen sulfate product are as follows:

U.S. Pat. No. 2,264,759 discloses the production of amino aliphatic hydrogen sulfates including aminoethyl hydrogen sulfate by reacting a hydroxy aliphatic amine with concentrated sulfuric acid in the presence of an organic solvent. Various solvents, e.g., hydrocarbons and chlorinated aromatic hydrocarbon solvents are added to the process to enhance the removal of water formed during the reaction. The addition of solvent to the reaction medium permitted distillation of water from the reaction medium at atmospheric pressure. Hydrogen sulfate salts of ethanolamine, triethanolamine, propanolamine and cyclohexylamine are shown.

U.S. Pat. No. 3,194,826 discloses a process for producing 2-aminoalkanol esters of sulfuric acid, particularly 2-aminoethyl hydrogen sulfate, by reacting monoethanolamine with sulfuric acid at temperatures from about 120°–200° C. Instead of removing all of the water from the reaction mixture prior to purification of the product some is retained to permit controlled crystallization.

U.S. Pat. No. 3,133,950 discloses a process for reacting an alkanolamine with sulfuric acid in the presence of a small amount of a cationic surface active agent. In an effort to force the reaction to completion, the reaction is carried out in the presence of an inert volatile solvent which is capable of forming an azeotrope with water. Representative cationic surface active agents include long chain quaternary ammonium compounds, fatty acid diamine condensates and fatty acid carbamides.

U.S. Pat. Nos. 4,330,480; 3,153,079 and 3,194,826 show variations on the above themes in the manufacture of aminoalkyl esters of sulfuric acid.

U.S. Pat. Nos. 3,169,143, 3,763,208 and 3,337,633 disclose the preparation of sulfuric acid esters of aminoalkanols, particularly 2-aminoethyl esters of sulfuric acid, by reacting an alkanolamine with sulfur trioxide. The '333 patent shows the preparation of sulfuric acid esters of ethoxy linear saturated secondary alcohols by reacting an ethoxy substituted alcohol with sulfamic acid.

SUMMARY OF THE INVENTION

This invention pertains to a process for selectively producing aminoethyl hydrogen sulfate by reacting ammonium sulfate or ammonium bisulfate with a condensation product of ethylene oxide and a poorly nucleophilic derivative of ammonia wherein the condensation product is represented by the formulas

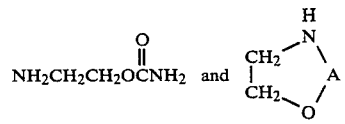

where A represents C=O or C=S.

A major advantage of the process is that the ammonium bisulfate reactant, in particular, is a by-product of many processes, e.g., a by-product of polyamine synthesis via the reaction of an aminoalkyl hydrogen sulfate with sodium hydroxide. A second advantage is that ammonium bisulfate is extremely effective as a sulfating agent for this reaction.

DETAILED DESCRIPTION OF THE INVENTION

By the process of this invention, ethylene compounds represented by either of the formulae

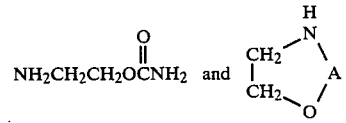

where A represents C=O or C=S can be converted to a valuable sulfate ester, i.e., aminoethyl hydrogen sulfate.

These compounds are typically carbamates, carboxamides, ureas or urethanes. All of these compositions contain a carbonyl group adjacent to a nitrogen or oxygen atom which is also attached to an ethylene radical. The carbonyl group is cleaved from the nitrogen or oxygen of the adjacent ethylene radical, thus permitting the formation of aminoethyl hydrogen sulfate. Representative compounds include 2-oxazolidinone, 2-oxazolidinethione, 2-aminoethyl carbamate N-phenyl-N'-(2-hydroxyethyl) urea, and N-methyl-N'-(2-hydroxyethyl) urea.

The sulfation of the condensation product of ethylene oxide and poorly nucleophilic derivatives of ammonia defined above is carried out under conditions sufficient to effect cleaving of the carbonyl group from the nitrogen or oxygen atom in the derivative. To do that, the reaction temperature will range from about 100°–200° C., and the pressure will range from vacuum to superatmospheric pressures, e.g. 100 atmospheres. Generally, atmospheric pressure to 100 psig is used.

Unlike typical sulfuric acid esterification processes, water is not always produced as a by-product. It depends upon the particular condensation or nucleophilic derivative used as a reactant. However, if prepared, water should be removed. Numerous water insoluble solvents which azeotrope with water can be utilized to remove the water from the system and to reduce viscosity of the reaction medium. Examples of suitable organic solvents include hydrocarbons, such as benzene, xylene, toluene, solvent naphtha, gasoline, isooctane, cyclohexane, and others. Chlorinated aromatic solvents are also suited, and these include chlorobenzene, orthodichlorobenzene, mixed chlorotoluenes, methylene chloride and the like. Representative solvents are shown in U.S. Pat. Nos. 2,264,759 and 4,330,480; these references are incorporated by reference.

The reaction between the sulfating agent and the condensation product of ethylene oxide and poorly nucleophilic derivatives of ammonia should be conducted under acidic conditions. By that it is meant the system should contain sufficient acid for neutralizing or capturing by-product ammonia as it is formed during the reaction. Therefore, in reaction mixtures where ammonium bisulfate is used as the reactant, the molar ratio of ammonium bisulfate to derivative should be at least 2:1, the extra mole of ammonium bisulfate being used to capture by-product ammonia. Normally, a mole ratio of 4–10 moles; ammonium bisulfate per mole of condensation product derivative is used. When less than 2 moles of ammonium bisulfate to derivative are used, conversion of the amine to the sulfate ester normally will cease when the reaction conditions move to a basic condition. Although conversions can be enhanced when the conditions are slightly basic by increasing temperature, e.g. to a level of about 200° C. to 260° C., the rate of conversion to the sulfate ester is slow and extensive charring of the product or reaction mixture can occur.

At the conclusion of the reaction, the product sulfate ester is recovered by conventional techniques. Typically, this involves distilling the water from the reaction medium and then cooling the reaction mixture and effecting crystallization of the product. As noted in the prior art, by appropriate application of heat and vacuum and by retaining sufficient water in the reaction mixture, one can achieve controlled crystallization of the product. Once the product is crystallized, then simple recovery techniques, such as centrifugation or filtration can be used to separate the product from the suspension. Hydrolysis of the product can be minimized during the crystallization of product by inclusion, in dilute concentration, e.g., 0.1–1% by weight based upon the weight of the water present in the system, of a water soluble salt of a weak acid. Examples of such salts include sodium acetate, sodium proprionate, sodium dihydrogen phosphate and the corresponding potassium counterparts. Other salts and techniques for reducing hydrolysis are disclosed in U.S. Pat. No. 3,037,042 and are incorporated by reference.

The following examples are provided to illustrate embodiments of the invention.

EXAMPLE 1

A series of runs were conducted to produce 2-aminoethyl hydrogen sulfate by the reaction of condensation products of ethylene oxide and poorly nucleophilic derivative of ammonia with ammonium bisulfate and ammonium sulfate. The following general procedure was utilized in producing 2-aminoethyl hydrogen sulfate.

A preselected quantity of ammonium bisulfate or ammonium sulfate was charged to a 250 ml 3-necked round bottom flask, fitted with a water-cooled condenser, and thermometer. Then, a preselected quantity of solvent and condensation product were charged to the flask and the flask sealed. At this point the contents were slowly heated to reflux temperature under constant agitation, to avoid "bumping" of the reaction mixture. The contents were then held at reflux temperature for a defined period of time, typically 1–4 hours, and the reaction terminated.

The product, 2-aminoethyl hydrogen sulfate, was recovered from the reaction mixture by crystallizing it from the solution and then drying the resulting solid in a vacuum oven. The samples were analyzed by 200 MHz proton NMR on an IBM SY-200 FT NMR spectrometer and by carbon-13 NMR on a Bruker WP-200FT NMR spectrometer.

Table 1, which follows, provides results for the reaction of either ammonium bisulfate or ammonium sulfate with 2-oxazolidinone at various feed molar ratios, conditions, etc., to produce 2-aminoethyl hydrogen sulfate. The quantities of ammonium sulfate or ammonium bisulfate and 2-oxazolidinone (OX) charged to the reactor, feed ratio, solvent, reaction time as indicated by various samples taken within the run and identified as A, B, etc., temperature (°C.), percent conversion, percent selectivity and yields are reported.

The percent conversion is expressed in units of mole percent by proton nuclear magnetic resonance analysis of the reaction mixture. Unless otherwise noted in the entry for selectivity, only 2-aminoethyl hydrogen sulfate (AES) and monoethanolammonium sulfate were present at the end of each reaction (by proton and carbon NMR). Owing to the rapidity of analysis, proton NMR was routinely used to characterize samples of reaction mixtures. The proton spectrum of AES exhibits triplets at 4.25 ppm ($\text{C}\underline{\text{H}}_2$—O; J=6 Hz) and 3.32 ppm ($\text{C}\underline{\text{H}}_2$—O; J=6 Hz); monoethanolammonium sulfate exhibits triplets at 3.78 ppm ($\text{CH}_2$—O; J=6 Hz) and 3.12 ppm ($\text{CH}_2$—O; J=6 Hz); 2-oxazolidinone exhibits triplets at 4.48 ppm ($\text{C}\underline{\text{h}}_2$—O; j=4.5 Hz) and 3.62 ppm ($\text{C}\underline{\text{h}}_2$—O; j=4.5 Hz). With 200 MHz proton nmr, signals for all the methylene groups were cleanly resolved. Conversion of 2-oxazolidinone to AES was judged by comparison of the average integrated signals for the methylene groups adjacent to both oxygen and nitrogen functionality of AES and monoethanolammonium sulfate, and 2-oxazolidinone. Conversion is expressed by:

$$\text{Conversion} = \frac{\overline{A}_{AES}}{\overline{A}_{AES} + \overline{A}_{monoethanolammonium\ sulfate} + \overline{A}_{2\text{-}oxazolidinone}} \times 100\%$$

$\overline{A}_{AES}$ = Average integrated area for AES
$\overline{A}_{monoethanolammonium\ sulfate}$ = Average integrated area for monoethanolammonium sulfate
$\overline{A}_{2\text{-}oxazolidinone}$ = Average integrated area for 2-oxazolidinone The percent selectivity was evaluated in units of mole percent by carbon NMR. Unless otherwise noted, only AES, 2-oxazolidinone, and monoethanolammonium sulfate were present at the end of each reaction; no by-products could be detected.

Yield is expressed in units of mole percent as the product of conversion times selectivity.

TABLE 1
PRODUCTION OF AES FROM 2-OXAZOLIDINONE (OX)

| Example | Ammonium Bisulfate (gm) | OX (gm)[a] | Feed Ratio (Molar)[b] | Solvent (ml) | Time (hr) | Temp (°C.) | Conversion % | Selectivity % | Yield % |
|---|---|---|---|---|---|---|---|---|---|
| 1 | 51.8 | 13.05 | 3/1 | Decane (125) | 0.5 | 174 | 79 | 100 | 79.1 |
|   |      |       |     |              | 2.0 | 100 | 31 | 100 | 31 |
| 2A | 57.5 | 10.9 | 4/1 | Nonane (125) | 0.25 | 151 | 8.6 | 100 | 8.6 |
| B  |      |      |     |              | 0.50 | 151 | 32.9 | 100 | 32.9 |
| C  |      |      |     |              | 1    | 151 | 78.0 | 100 | 78.0 |
| D  |      |      |     |              | 2    | 151 | 100.0 | 100 | 100.0 |
| 3A | 57.5 | 10.9 | 4/1 | Mesitylene (125) | 1 | 100 | 100.0 | 100 | 100.0 |
| B  |      |      |     |              | 2    | 100 | 100.0 | 100 | 100.0 |
| 4A | 28.8 | 5.4 | 4/1 | None; nitrogen purge | 1 | 165 | 62.6 | 100 | 100.0 |
| B  |      |     |     |              | 2.5 | 165 | 91.1 | 100 | 91.1 |
| 5A | 115.0 | 10.9 | 8/1 | Nonane (125) | 0.25 | 151 | 11.2 | 100 | 11.2 |
| B  |       |      |     |              | 0.50 | 151 | 33.5 | 100 | 33.5 |
| C  |       |      |     |              | 0.75 | 151 | 61.1 | 100 | 61.1 |
| D  |       |      |     |              | 1    | 151 | 71.5 | 100 | 71.5 |
| E  |       |      |     |              | 2    | 151 | 86.5 | 100 | 86.5 |
| 6A | 17.3 | 8.7 | 1.5/1.0 | Mesitylene (125) | 0.25 | 168 | 100 | 100 | 79.1 |
| B  |      |     |         |                  | 0.50 | 168 | 100 | 100 | 65 |
| C  |      |     |         |                  | 1.0  | 168 | 100 | 100 | 80 |
| D  |      |     |         |                  | 2.0  | 168 | 100 | 100 | 80 |

Comments on Production of AES from 2-oxazolidinone with Ammonium Bisulfate

If the initial mole ratio of ammonium bisulfate/2-oxazolidinone is less than 2:1, conversion of 2-oxazolidinone and monoethanolammonium sulfate to AES is incomplete (see Example 6). Incomplete conversion results from failure to maintain an acidic reaction medium.

For mole ratios of ammonium bisulfate/2-oxazolidinone above 2:1, high yields of AES are obtained within 1–2 hours. With a 4:1 mole ratio of ammonium bisulfate/2-oxazolidinone, increasing reaction temperatures provide increasing conversions to, and yields of, AES (cf. Examples 2 and 3). However, use of increasing levels of excess ammonium bisulfate at a constant temperature appears to offer little advantage. Although good yields of AES may be obtained, complete conversion of 2-oxazolidinone to AES may be retarded, owing to dilution of the reaction mixture by the excess ammonium bisulfate (cf. Examples 2 and 5).

Inclusion of a solvent to aid temperature control is unnecessary; the reaction mixture may be agitated with a stream of nitrogen (see Example 4).

EXAMPLE 2

Preparation of AES from 2-aminoethyl carbamate. The procedure of Example 1 was repeated except that the desired quantity of ammonium bisulfate is charged to a 250 ml three-necked round bottom flask equipped with a large egg shaped stirrer. The desired quantity of the appropriate solvent (see Table 2) is then added to the flask, and the flask is fitted with a Dean-Stark receiver and a water-cooled condenser. A thermometer is fitted to the central neck of the reaction flask, and an addition funnel is placed in the remaining neck of the flask. The desired quantity of 2-aminoethylcarbamate (prepared according to the procedure of W. F. Tousignant and A. W. Baker, *J. Org. Chem.*, 22, 166 (1957) from urea and ethylene oxide; a 2-aminoethylcarbamate product, mixed with approximately 10–15 weight percent of the isomeric 2-hydroxyethyl urea, is obtained.) The resulting product is dissolved in water to provide a solution containing 33% 2-aminoethylcarbamate by weight. The solution is placed in the addition funnel. The mixture of organic solvent and ammonium bisulfate is heated to reflux temperature with stirring, and the solution of 2-aminoethycarbamate added carefully to prevent bumping. Upon completion of the addition, the addition funnel is removed from the reaction flask, and replaced with a ground glass stopper. Samples were removed from the reaction mixture at the times indicated in Table 2 for each example. Analyses were carried out by 200 MHz proton nmr on an IBM SY-200 FT NMR and by carbon-13 nmr on a Bruker WP-200 FT NMR Spectrometer.

TABLE 2
PRODUCTION OF AES FROM 2-AMINOETHYLCARBAMATE

| Run | Ammonium Bisulfate (gm) | NAEA (gm) | Feed Ratio (molar) | Solvent (ml) | Time (hr) | Temp (°C.) | Conversion (%) | Selectivity (%) | Yield (%) |
|---|---|---|---|---|---|---|---|---|---|
| 1A | 56.7 | 12.8 | 4/1 | Mesitylene (125) | 0.25 | 1168 | 81 | 100 | 81 |
| B  |      |      |     |                  | 0.50 | 168 | 81 | 100 | 81 |
| C  |      |      |     |                  | 1.00 | 168 | 90 | 100 | 90 |
| D  |      |      |     |                  | 1.50 | 168 | 92 | 100 | 92 |
| 2A | 56.7 | 6.4 | 8/1 | Mesitylene (125) | 0.25 | 168 | 95 | 100 | 95 |
| B  |      |     |     |                  | 0.50 | 168 | 100 | 100 | 100 |
| C  |      |     |     |                  | 1.00 | 168 | 100 | 100 | 100 |
| D  |      |     |     |                  | 1.50 | 168 | 100 | 100 | 100 |

The following pertains to Table 2.
(a) 2-Aminoethylcarbamate
(b) Ratio of moles of ammonium bisulfate to moles of 2-aminoethylcarbamate.
(c) Evaluated in terms of mole percent by proton nuclear magnetic resonance analysis of reaction mixtures. AES and monoethanolammonium sulfate were the only species present at the end of each reaction (by proton and carbon nmr). Owing to the rapidly of analysis, proton nmr was routinely used to characterize samples of reaction mixtures. The proton spectrun of AES exhibits triplets at 4.26 ppm ($CH_2$—O; J=6 HZ) and 3.32 ppm ($CH_2$—N; J=6 Hz), while that of monoethanolammonium sulfate exhibits triplets at 3.78 ppm ($CH_2$—O; J=6 Hz) and 3.12 ppm ($CH_2$—O; J=6 HZ) and 3.12 ppm ($CH_2$—O; J=6 Hz). With 200 MHz proton nmr, signals for all the methylene groups were clearly resolved. Conversion of 2-aminoethylcarbamate to AES was judged by comparison of the average integrated signals for the methylene groups adjacent to both oxygen and nitrogen functionality for AES and monoethanolammonium sulfate. Conversion is expressed by:

$$\text{Conversion} = \frac{\overline{A}_{AES}}{\overline{A}_{AES} + \overline{A}_{monoethanolammonium\ sulfate}} \times 100\%$$

$\overline{A}_{AES}$ = Average integrated area for AES
$\overline{A}_{monoethanolammonium\ sulfate}$ = Average integrated area for monoethanolammonium sulfate (d) Evaluated in units of mole percent by carbon NMR. Only AES and monoethanolammonium sulfate were present at the end of each reaction; no by-products could be detected.

(e) Expressed in terms of mole percent as the product of conversion times selectivity.

Comments on Production of AES from 2-Aminoethylcarbamate

For mole ratios of ammonium bisulfate/aminoethylcarbamate of 4:1 and 8:1, high yields of AES are obtained within 1-1.5 hours. Conversion of aminoethylcarbamate to AES occurs more rapidly at the higher ammonium bisulfate/aminoethylcarbamate feed ratio. In the absence of an acidic sulfate, production of AES cannot be detected.

What is claimed is:

1. A process for producing aminoethyl hydrogen sulfate under acidic conditions by reacting ammonium bisulfate or ammonium sulfate with an ethylene compound represented by the formulae:

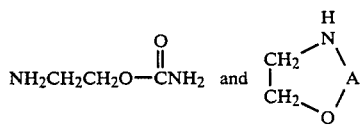

where A represent C=O or C=S.

2. A process for producing aminoethyl hydrogen sulfate by reacting ammonium bisulfate with an ethylene compound selected from the group consisting of 2-oxazolidinone, 2-oxazolidinethione and 2-aminoethyl carbamate under acidic conditions at a temperature from 100°-200° C., said acidic conditions being maintained by utilizing a mole ratio of said ammonium bisulfate to said ethylene compound of 2-10:1.

3. The process of claim 2 wherein the reaction is carried out in the presence of an organic water insoluble solvent which is capable of forming an azeotrope with water at the reaction temperature.

4. The process of claim 3 wherein the reaction is carried out at pressures from atmospheric pressure to 100 psig.

5. The process of claim 4 wherein said ethylene compound is 2-oxazolidinone.

6. The process of claim 4 wherein said ethylene compound is 2-aminoethyl carbamate.

7. The process of claim 4 wherein said acidic conditions are maintained by utilizing a molar ratio of ammonium bisulfate or ammonium sulfate to ethylene compound within a range of 4-10:1.

* * * * *